(12) United States Patent
Liao et al.

(10) Patent No.: US 7,906,333 B2
(45) Date of Patent: Mar. 15, 2011

(54) SURFACE MODIFICATION OF POLYSACCHARIDE, THE MODIFIED POLYSACCHARIDE, AND METHOD OF CULTURING AND RECOVERY CELLS USING THE SAME

(75) Inventors: Chun-Jen Liao, Taipei (TW);
Yung-chih Wu, Taipei County (TW);
Chen-Chi Tsai, Taipei County (TW);
Hsiang-Ming Huang, Taipei (TW);
Yuan-Hua Hsu, Taichung (TW);
Shu-Fang Chiang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 11/384,386

(22) Filed: Mar. 21, 2006

(65) Prior Publication Data
US 2007/0148768 A1    Jun. 28, 2007

(30) Foreign Application Priority Data
Dec. 27, 2005   (TW) ............................. 94146698 A

(51) Int. Cl.
*C12N 5/00*   (2006.01)
*A61K 31/715*   (2006.01)
(52) U.S. Cl. .......... 435/402; 435/395; 424/491; 424/493
(58) Field of Classification Search .................. 435/395, 435/402; 424/491, 493
See application file for complete search history.

(56) References Cited

U.S. PATENT DOCUMENTS

| | | | |
|---|---|---|---|
| 2,965,498 A * | 12/1960 | Hartwig et. al. | 426/277 |
| 3,349,079 A * | 10/1967 | Freedman | 536/3 |
| 3,842,062 A * | 10/1974 | Eastman | 530/411 |
| 4,614,794 A * | 9/1986 | Easton et al. | 530/356 |
| 5,254,471 A | 10/1993 | Mori et al. | |
| 5,529,914 A | 6/1996 | Hubbell et al. | |
| 5,801,033 A | 9/1998 | Hubbell et al. | |
| 5,916,790 A * | 6/1999 | Enevold | 435/178 |
| 6,054,142 A | 4/2000 | Li et al. | |
| 6,103,269 A | 8/2000 | Wunderlich et al. | |
| 6,171,610 B1 | 1/2001 | Vacanti et al. | |
| 6,231,879 B1 | 5/2001 | Li et al. | |
| 6,306,169 B1 | 10/2001 | Lee et al. | |
| 6,334,968 B1 | 1/2002 | Shapiro et al. | |
| 6,425,918 B1 | 7/2002 | Shapiro et al. | |
| 6,471,993 B1 | 10/2002 | Shastri et al. | |
| 6,596,296 B1 | 7/2003 | Nelson et al. | |
| 6,656,508 B2 | 12/2003 | Goldenberg et al. | |
| 6,790,455 B2 | 9/2004 | Chu et al. | |
| 6,793,675 B2 | 9/2004 | Shapiro et al. | |
| 6,858,222 B2 | 2/2005 | Nelson et al. | |
| 6,911,227 B2 | 6/2005 | Hubbell et al. | |

OTHER PUBLICATIONS

Hermes et al. 2002. Polymeric alginate films and alginate beads for the controlled delivery of macromolecules. Trends Biomater. Artif. Organs. vol. 15(2):54-56.*
Kuo et al. 2001. Ionically crosslinked alginate hydrogels as scafolds for tissue engineering: Part 1. Structure, gelation rate and mechanical properties. Biomaterials. 22:511-521.*
Sodium Alginate. 2009. FAO Corporate Document Repository. http://www.fao.org/docrep/W6355E/w6355e0x.htm. p. 1-3.*

* cited by examiner

*Primary Examiner* — Taeyoon Kim
(74) *Attorney, Agent, or Firm* — Birch, Stewart, Kolasch & Birch, LLP

(57) ABSTRACT

A surface modification method of polysaccharide, the modified polysaccharide, and a method of culturing and recovery cells using the same are provided. The surface modification method of polysaccharide comprises (a) immersing a polysaccharide material in an acid, (b) immersing the polysaccharide material in an acidic solution containing a protein, and (c) immersing the polysaccharide material in an alkaline solution containing bivalent metal ions.

14 Claims, 20 Drawing Sheets

2 days 3 days 7 days 6 hours 24 hours 7 days 6 hours 24 hours 7 days

US 7,906,333 B2

SURFACE MODIFICATION OF POLYSACCHARIDE, THE MODIFIED POLYSACCHARIDE, AND METHOD OF CULTURING AND RECOVERY CELLS USING THE SAME

BACKGROUND OF THE INVENTION

1. Field of the Invention

The present invention relates to surface modification of polysaccharide, and in particular to mechanically embedding protein into the surface of polysaccharide to enhance cell attachment thereto.

2. Description of the Related Art

Mass cell production is important in tissue engineering, protein drug production, and cell therapy. Conventional mass cell production technology includes static flat culturing and dynamic bioreactor culturing. Static flat culturing is appropriate for small-scale trials such as $10^6$-$10^8$ cells cultured in laboratory or factory. To compensate for the limited surface of the culture plate, large-scale cultures require numerous culture plates, however, manual operations such as seeding cells, changing media, passaging or harvesting cells increases labor burden and the risk of contamination. It is, therefore, not economical for mass production of animal cells.

Bioreactors provide sufficient metabolic exchanges and are popular in mass production of animal cells. Adherent cells cultured in bioreactor can be two- or three-dimensional. The former provides solid micro-beads for cells to attach to beads' surface with a two-dimensional manner and also evenly distributed nutrients. There are some drawbacks in this culture system. For example, cells will be dedifferentiation, much more shear stress effect, and friction is produced by stirring in the bioreactor. The latter provides porous matrices for cells to attach to porous contracture with a three-dimensional manner and provides more space for cell growth and less shear stress, although harvesting cells can be impeded. The proliferated cells may aggregate, and they will impede harvesting cells by regular digesting enzyme. For harvesting enough cell number, the longer digestion time is required, however, it will injure cells and reduce the recovery rate of healthy cells.

Most of mammalian cells are adherent, the growth of which includes attachment, propagation, and extension. Appropriate adherent materials may shorten attachment time for the cells to advance to log phase, increasing production efficiency and improving cell quality. Mass production of mammalian cells requires optimal media, appropriate mass transfer, low shear stress, and suitable carriers. Among these, cell carriers present the most critical issue. For long term cultivation of adherent cells in a bioreactor, various insoluble and porous carriers have been developed. These carriers are not designed to be implanted into living subjects and can be artificial polymers such as polystyrene (PS), polyvinyl chloride (PVC), or polymethyl acrylate resin. For example, U.S. Pat. No. 5,254,471 discloses a carrier for cell cultures comprising polyester fibers. The carrier makes it possible for the cells to retain their differentiation and proliferation ability for a long time, however, cell recovery from the carrier can be a problem. Carriers for cell recovery include two strategies. The cells can be embedded into a hydrogel and cultivation is performed in a hollow fiber bioreactor or a co-axial bioreactor. While cells can be recovered easily, the growth thereof may be suppressed by the low mass transfer of the carrier, imbedding long term cultivation. Cell recovery can be achieved by enzyme digestion such as trypsin digestion, but with inherent low recovery rate with high cell mortality. It is, therefore, important to develop a carrier having both insoluble and soluble properties for tissue engineering.

Developed carriers are mainly applied as implants or sustained-release carriers, rarely for cell cultivation. For example, U.S. Pat. No. 6,790,455 discloses a biodegradable and/or bioabsorbable fibrous matrix formed by biodegradable and/or bioabsorbable PLA/PLG/HA for delivering viable cells to a mammal using the cell storage and delivery system. U.S. Pat. No. 6,171,610 discloses a permeable, biocompatible support structure of PEO/PPO/PMA/PVA with a hydrogel-cell composition including a hydrogel, such as alginate, and tissue precursor cells. U.S. Pat. No. 6,656,508 discloses a sustained-release gel bead composition comprising PEG-alginate. U.S. Pat. Nos. 6,596,296 and 6,858,222 disclose bioabsorbable PLGA fiber for drug delivery. U.S. Pat. No. 6,103,269 discloses a thermoreversible sol/gel for releasing active agents. U.S. Pat. No. 6,471,993 discloses biocompatible PLLA/PGA/PEG/PMMA matrix for cell cultivation. U.S. Pat. Nos. 6,054,142 and 6,231,879 disclose a biocompatible cell device having an internal foam scaffold to provide a growth surface for encapsulated cells which produces a biologically active molecule. Most of these disclosures use insoluble cell matrix or gel for tissue transplant or drug release with no consideration for cell recovery.

A newly introduced matrix material is alginates, a family of unbranched polysaccharides with properties that vary widely depending on composition. For example, U.S. Pat. No. 4,614,794 (1986) discloses a complex of alginate and collagen for the formation of wound dressings and surgical implants. In addition, U.S. Pat. Nos. 5,529,914, 5,801,033, and 6,911,227 (1996) disclose a method for the formation of biocompatible membranes around biological materials using photopolymerization of water soluble molecules such as alginate or collagen, with no usage of cell culture. U.S. Pat. No. 6,306,169 (2001) discloses a biomechanical implant comprising collagen and a hydrated alginate gel, however, this implant is not for cell culture. U.S. Pat. Nos. 6,334,968, 6,425,918, and 6,793,675 (2002) disclose a method of forming polysaccharide sponges for cell culture and transplantation. A polysaccharide solution containing alginate is subjected to gelation to form a polysaccharide gel, and the gel is lyophilized to obtain a polysaccharide sponge.

The disclosed carriers still experience poor cell growth and low cell recovery rate, such that a need remains to develop a carrier which provides appropriate growth conditions and high cell recovery rate.

BRIEF SUMMARY OF THE INVENTION

A detailed description is given in the following embodiments with reference to the accompanying drawings.

An embodiment of the invention provides a surface modification method of polysaccharide. The method comprises immersing a polysaccharide material in an acid, immersing the polysaccharide material in an acidic solution containing a protein, and immersing the polysaccharide material in an alkaline solution containing bivalent metal ions.

Also provided is a modified polysaccharide for cell culture prepared by the disclosed method. The modified polysaccharide can be a film, a microbead, or a porous matrix.

Further provided is a method of culturing and recovering cells using the modified polysaccharide. The method comprises seeding cells into the modified polysaccharide, cultivating the cells, dissolving the modified polysaccharide in an ion chelating agent, and collecting the cells.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the subsequent detailed description and accompanying drawings, which are given by way of illustration only, and thus are not limitative of the present invention, and wherein:

FIG. 6A, 6D are blank control; FIG. 6B, 6E are unmodified film; FIG. 6C, 6F are collagen-modified film.

FIG. 7A is blank control; FIG. 7B is unmodified film; FIG. 7C is collagen-modified film.

FIG. 8A, 8C, 8E are unmodified microbeads; FIG. 8B, 8D, 8F are collagen-modified microbeads. FIG. 8A, 8B are 2-day cultivation; FIG. 8C, 8D are 3 days; FIG. 8E, 8F are 7 days.

FIGS. 10A, 10D, and 10G are control; FIGS. 10B, 10E, and 10H are unmodified film; FIGS. 10C, 10F, and 10I are collagen-modified film. FIG. 10A, 10B, 10C are 6-hour incubation; FIG. 10D, 10E, 10F are 24 hours; FIG. 10G, 10H, 10I are 72 hours.

FIG. 11A, 11D, 11G are control; FIG. 11B, 11E, 11H are the unmodified film; FIG. 11C, 11F, 11I are the collagen-modified film. FIG. 11A, 11B, 11C are 6-hour incubation; FIG. 11D, 11E, 11F are 24 hours; FIG. 11G, 11H, 11I are 72 hours.

DETAILED DESCRIPTION OF THE INVENTION

Figure 1:
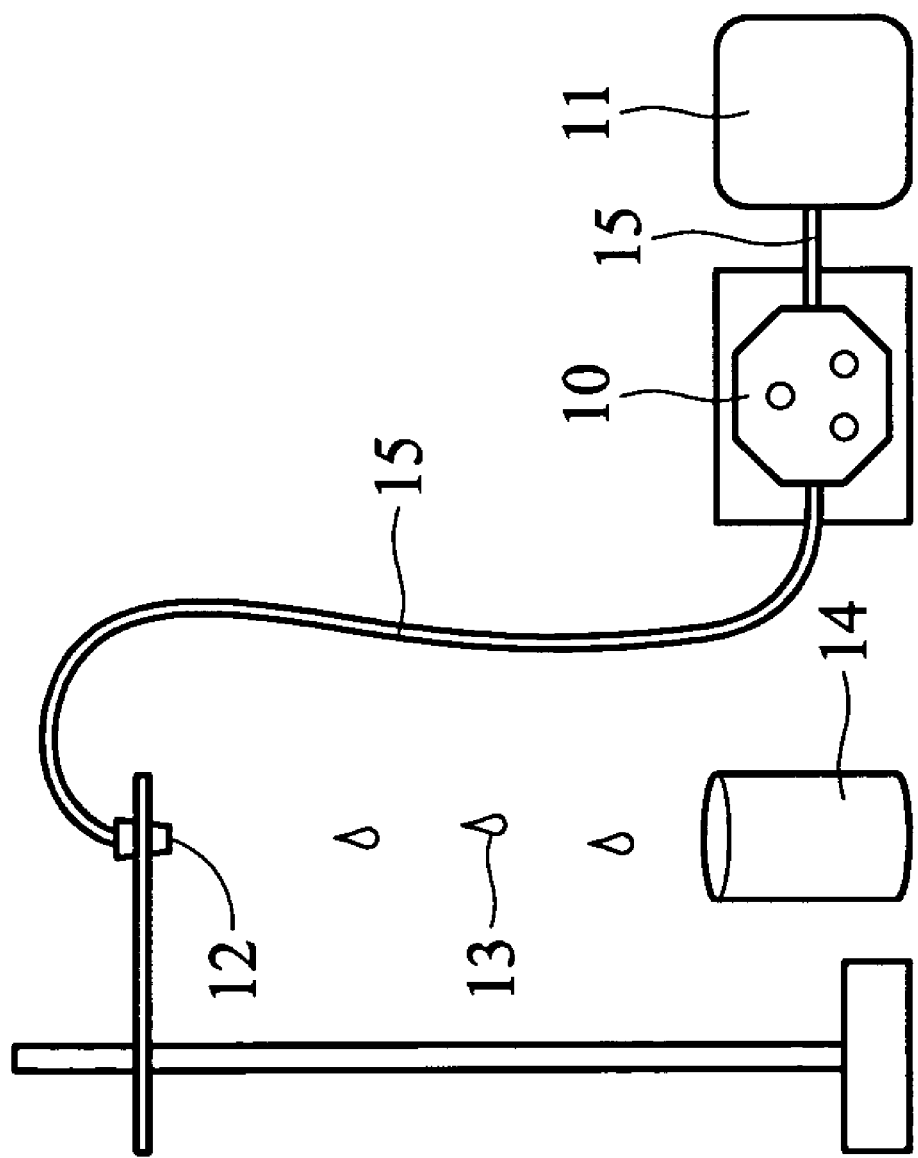
FIG. 1 is a diagram of a device for preparation of microbeads in an embodiment of the invention.

The following description is of the best-contemplated mode of carrying out the invention. This description is made for the purpose of illustrating the general principles of the invention and should not be taken in a limiting sense. The scope of the invention is best determined by reference to the appended claims.

A surface modification method of polysaccharide, the modified polysaccharide, and a method of culturing and recovery cells using the same are provided.

The surface modification method of polysaccharide adopts the solubility and segregation effects of the polysaccharide in acidic or alkaline solutions and ionic crosslink reaction to mechanically embed a protein into the surface of a solid polysaccharide, such as alginate, enhancing cell attachment of the polysaccharide without changing the reversible ionic crosslink thereof. When cells are proliferated on the modified polysaccharide, collection of the cells can be accomplished by dissolving the polysaccharide with an ion chelating agent. The ion chelating agent may capture calcium ions in the polysaccharide and the solid polysaccharide will gradually dissolve into a soluble form. The solution containing the cells and the dissolved polysaccharide is subjected to centrifugation to separate the cells from the dissolved polysaccharide. The cells proliferated on the modified polysaccharide can thus be completely harvested.

Alginate produced by brown seaweeds is a linear, unbranched polysaccharide composed of 1,4-linked β-D-mannuronic acid (M) and α-L-guluronic acid (G). Depending on the source algae, alginates may have different M/G ratio, leading to various conformational preferences and behaviors. Gel formation of alginate is a reversible reaction and can be achieved by adding divalent cations such as calcium ion or dissolved by adding an ion chelating agent such as EDTA. The inventors have developed a three-dimensional porous matrix composed of alginate for the cultivation of anchorage-dependent cells. After the cells are proliferated in the matrix, collection of the cells can be accomplished by dissolving the matrix with an ion chelating agent. The ion chelating agent captures calcium ions in the alginate gel and dissolves the alginate gel into a soluble form. The solution containing the cells and the dissolved alginate is subjected to centrifugation to separate the cells from the dissolved alginate. The cells proliferated on the alginate can be completely harvested. Cells and negatively charged proteins cannot, however, be easily attached on the surface of alginate due to the presence of $COO^-$ ions. To improve the hydrophilic property of alginate, chemical modification can be applied, such as using hydrophobic functional groups, positive charged compounds, or protein functional groups. However, the chemical modification usually employs functional groups with strong reactive properties or compounds with high positive charge, and the modified alginate may experience cell toxicity or lose the reversible capability of gel formation. The invention utilizes the protonization properties of the alginate in an acidic solution. Calcium ions and sodium ions of the alginate can be washed out without deforming the structure of the alginate. The protonized alginate is immersed in an acidic solution containing proteins such as collagen or chitosan to embed the proteins into the surface of the alginate. The alginate is then cross-linked by an alkaline solution such as calcium hydroxide solution to solidify the alginate and segregate the proteins on the surface of the alginate. With the solubility and segregation effects of the alginate in acidic or alkaline solutions and ionic crosslink reaction, protein can be mechanically embedded into the surface of the alginate gel, enhancing the cell attachment of the alginate.

Accordingly, an embodiment of a surface modification method of polysaccharide comprises immersing a polysaccharide material in an acid, immersing the polysaccharide material in an acidic solution containing a protein, and immersing the polysaccharide material in an alkaline solution containing bivalent metal ions.

The polysaccharide can be, but is not limited to, alginate, N,O-carboxymethyl chitosan, or carboxymethyl cellulose, preferably alginate. In addition, the polysaccharide can be a film, a microbead, or a porous matrix, with thickness of the film 20 to 5000 μm, microbead particle size is 20 to 2000 μm in diameter, and pore size of the matrix is 20 to 2000 μm with porosity of 30% to 95%.

The protein can be, but is not limited to, collagen, gelatin, or chitosan, preferably collagen.

The alkaline solution containing bivalent metal ions can be, but is not limited to, calcium hydroxide, magnesium hydroxide, or strontium hydroxide, preferably calcium hydroxide.

Also provided is a modified polysaccharide embedded with a protein on the surface thereof. The modified polysaccharide is prepared by the method disclosed and can be a film, a microbead, or a porous matrix for cell culture.

Further provided is a method of culturing and recovering cells using the modified polysaccharide. The method comprises seeding cells into the modified polysaccharide, cultivating the cells, dissolving the modified polysaccharide in an ion chelating agent, and collecting the cells.

In an embodiment of the method of culturing and recovering cells using the modified polysaccharide, cells are suspended in a medium to form a cell suspension. The cells are anchorage-dependent and can be, but are not limited to, liver cells, fibroblasts, cartilage cells, Vero cells, CHO cells, osteoblasts, bone marrow cells, or umbilical blood cells. The cell suspension is seeded into a solution comprising the modified polysaccharide and cultured under suitable conditions, such as in a static flat culturing system or a dynamic bioreactor culturing system, or the cells can be cultured first in a static flat culturing system and then in a dynamic bioreactor culturing system.

The ion chelating agent can include, but is not limited to, EDTA (ethylenediminetetraacetic acid), sodium citrate, or EGTA (ethyleneglycol-bis(2-aminoethylether)-N',N',N',N'-tetraacetic acid), preferably EDTA. The concentration of EDTA can be 50 to 300 mM, or the concentration of sodium citrate can be 50 to 500 mM.

Practical examples are described herein.

EXAMPLES

Example 1

Preparation of a Film Modified with Collagen

Two percent alginate aqueous solution was prepared, poured on the surface of a glass substrate, and evenly distributed thereon with a scraper. The alginate aqueous solution on the glass substrate was dried in an oven at 50° C. After the alginate solidified, the glass substrate with the alginate film was immersed in 1% $CaCl_2$ aqueous solution to introduce calcium ions for cross-linking. The alginate film was removed from the glass substrate and washed with $dH_2O$ several times.

The film was immersed in 0.6N of HCl aqueous solution for 8 hours, then in 2 mg/ml of collagen in 50 mM acetic acid solution for 8 hours, and in 1% calcium hydroxide solution for 1 hour neutralization and solidification. The film was then washed with $dH_2O$ to remove calcium hydroxide. The film was sliced into circular pieces with a diameter of 14 mm for subsequent steps.

Example 2

The Preparation of Microbeads Modified with Collagen

One percent alginate aqueous solution was cross-linked with 1% calcium chloride aqueous solution by spray. The device used for the preparation of alginate microbeads is shown in FIG. 1. Alginate solution 11 was passed through a conduit 15 driven by a peristaltic pump 10 to generate alginate microbeads 13 through a spray nozzle 12. The alginate microbeads 13 were collected in a calcium chloride solution 14 for 2-hour cross-linking. Alginate microbeads with a diameter of 100 μm to 400 μm were collected with a sieve and placed in 0.6N of HCl aqueous solution overnight. On the second day, the alginate microbeads were immersed in 2 mg/ml of collagen solution for 3 hours for coating of collagen onto the surface thereof. Neutralization was performed with calcium hydroxide solution for 30 hours. The collagen-modified alginate microbeads were washed with 10% alcohol 3 times for 1 hour each time, and stored in 70% alcohol.

Figure 2:
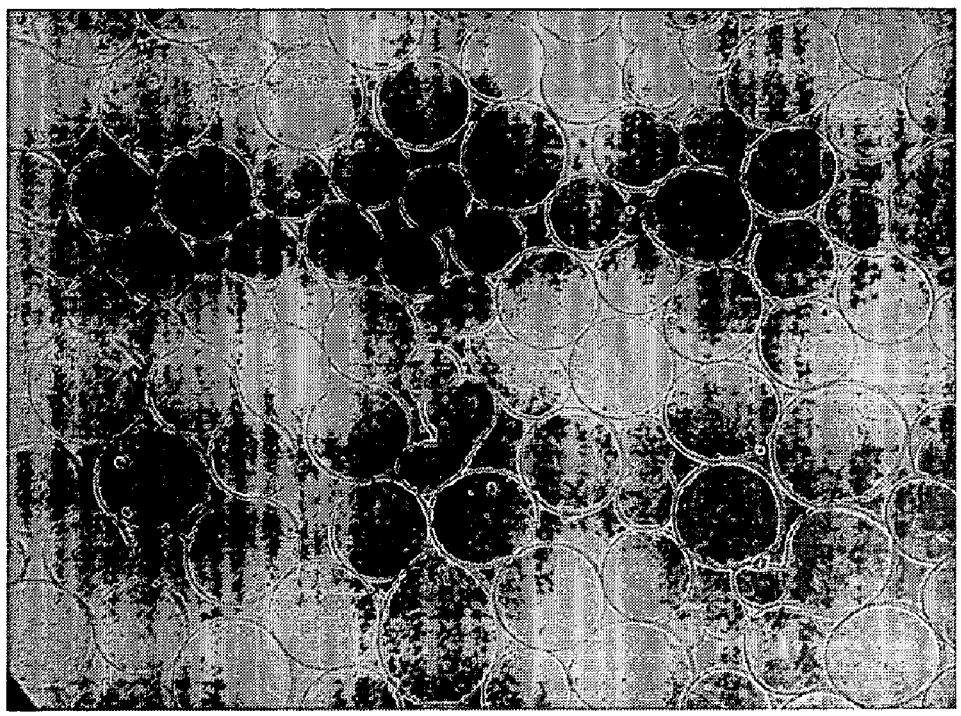
FIG. 2 is a microscopic photograph of collagen-modified microbeads in the embodiment of the invention.

The microbeads were examined with a laser diffraction particle size analyzer. The results are shown as a microscopic photograph in FIG. 2. The average size of the microbeads is 147±28 μm.

Example 3

The Preparation of Porous Matrix Modified with Collagen

In brief, soluble alginate was admixed with calcium phosphate particles to form a mixture. For an even distribution of calcium phosphate, the mixture was placed into a mold as disclosed in U.S. Pat. No. 6,436,426, incorporated by reference. Calcium ion solution was introduced into the mixture to perform cross linking, and calcium phosphate was dissolved by acid to leave a plurality of voids in the mixture.

The calcium phosphate particles were prepared from a compact section of cattle thighbone heat-treated at 900° C. to remove organic components and decarbonized to obtain inorganic calcium phosphate. A lump of inorganic calcium phosphate was then pulverized in a disintegrator. The particles were passed through a sieve of 40~60 mesh to obtain calcium phosphate particles between 250~420 μm for the following procedure. The solution used for cross linking was 1% calcium chloride aqueous solution.

Figure 3:
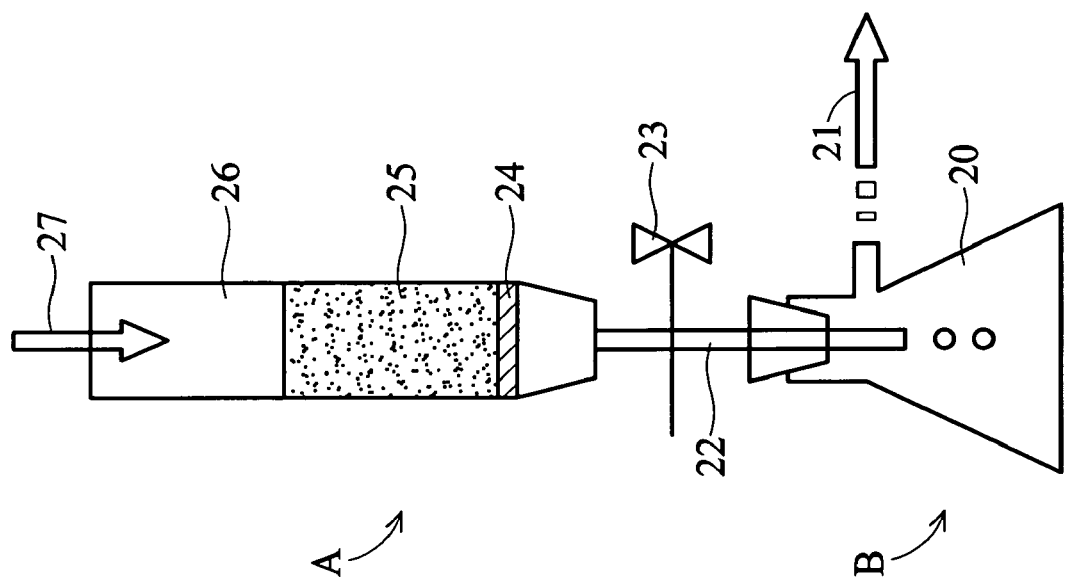
FIG. 3 is a diagram of a filtration system for preparation of a porous matrix in an embodiment of the invention.

Appropriate amounts of deionized water were added to 17.14 g of calcium phosphate particles with excess water removed by vacuum filtration to a final water content of 14.6±3.2%. 0.98 g of sodium alginate powder (low viscosity, Mw: 12,000~80,000, Sigma Chemical Co.) was admixed with the hydrous calcium phosphate particles and 12.86 g of anhydrous calcium phosphate particles to form a mixture of calcium phosphate particles and sodium alginate. The mixture was poured into the device shown in FIG. 3, comprising a filtration unit A and a connected suction unit B, providing pressure difference. The filtration unit A comprises a filtration vessel 26 containing the mixture of sodium alginate powders and calcium phosphate particles 25, a filter film 24, a valve 23 controlling a filtrate flowing in the filtration vessel 26, a filtrate conduit 22 for the filtrate flow, and a filtrate vessel 20 receiving the filtrate.

One percent calcium chloride aqueous solution (Sigma Chemical Co.) 27 was added to the mixture in the filtration vessel 26 for cross linking between calcium phosphate and sodium alginate. Vacuum unit B provided pressure difference for surplus solution, generating cross-linking between the surface of calcium phosphate particles and the partially dissolved sodium alginate. Mark 21 indicates negative pressure. The solidified matrix was removed to a beaker with 0.6N HCl solution. The HCl solution was replaced every day at room temperature. The matrix was stirred in the HCl solution for three days to wash out calcium phosphate particles, then in 2 mg/ml collagen in 50 m M acetic acid solution for 8 hours. The matrix was placed in 1% calcium hydroxide solution for neutralization and solidification. After 1 hour, calcium hydroxide solution in the matrix was washed out by deionized water, and a porous matrix obtained.

The obtained porous matrix was sliced into round tablets 5 mm in diameter and 3 mm in thickness. The pore size of the porous matrix was tested according to ASTM D-3576-94 and porosity measured by Optimas Image Analysis Software Version 6.5 (Media Cybermetics, L.P.) The microstructure of the porous matrix was observed under scanning electron microscope, operated at a current of 40 mA.

Results show pore size of the porous matrix of 317±153 μm, with porosity 87.4±5.4%. Pore distribution of the porous matrix was uniform and the pores interconnected.

Example 4

Analysis of the Surface Collagen Content of the Modified Alginate

Figure 4A:
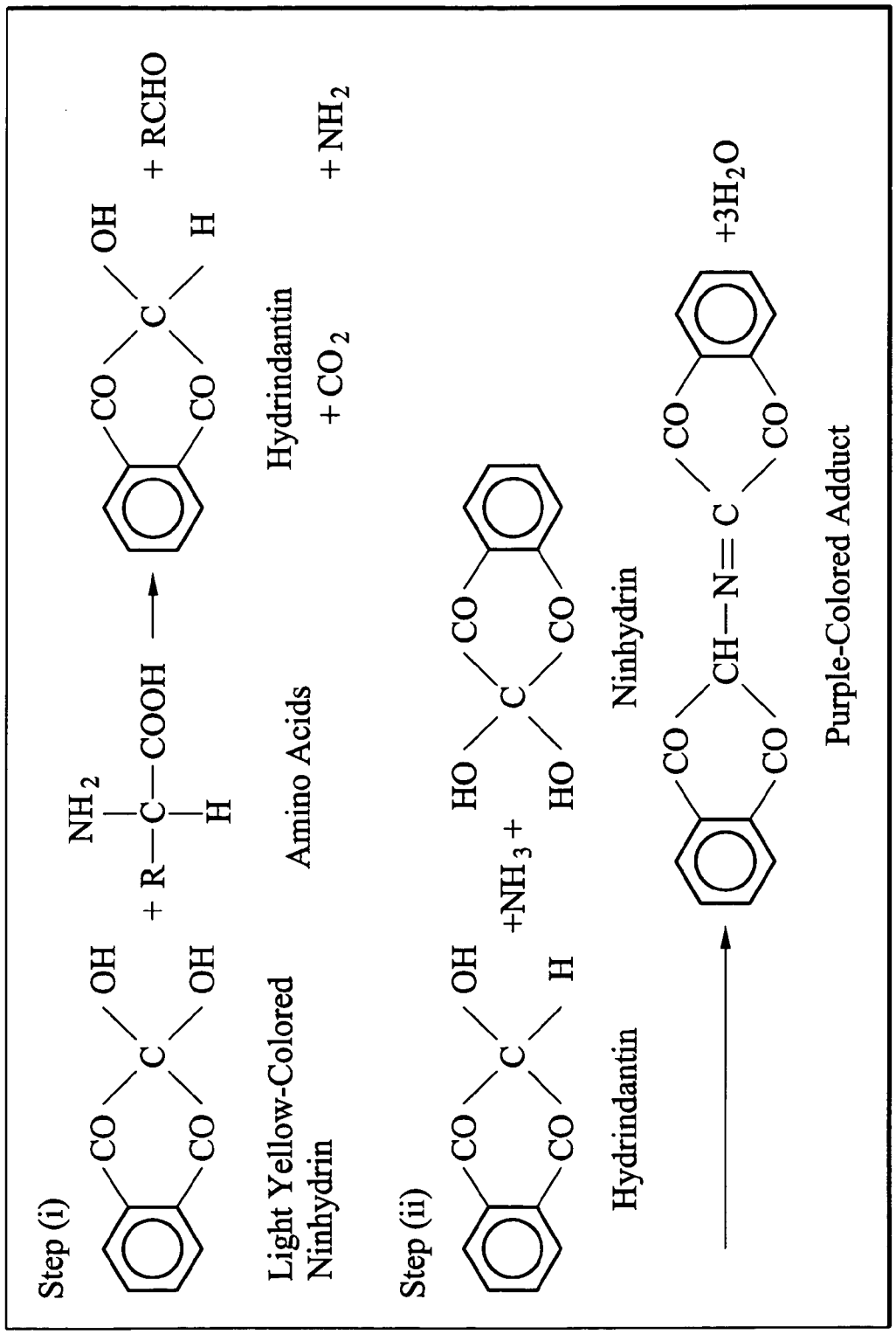
FIG. 4A is a schematic view of a ninhydrin reaction for determination of the amount of collagen on a surface of the embodiment of the matrix.

Collagen has a repeat amino acid structure of -Gly-X—Y— where X is proline and Y is hydroxyproline, and a constant —$NH_2$ content in collagen molecule can be expected (Mathews, C. K, Van Hold, K. E, Biochemistry $2^{nd}$ Edition, The Benjamin/Cummings Publishing Company, Inc. California, 1995.) The collagen content of the modified alginate can, therefore, be determined from the —$NH_2$ content detection. Ninhydrin detection was applied, based on reaction of ninhydrin and free amino groups producing a purple product, as shown in FIG. 4A. The purple product can be detected at 570 nm to determine the amount of free amino groups.

Collagen-modified alginate structures including films, microbeads, and porous matrices were vacuum dried for 24 hours. Three mg of the samples were immersed in water for 1 hour and ninhydrin reagent then added. The reaction was performed at 100° C. for 20 min. The results were read by a microplate reader (Molecular Devices/SPECTRAmaz 340PC384) at 570 nm. The collagen content of the modified alginate was calculated by the comparison of the results and the standard curve.

Figure 4B:
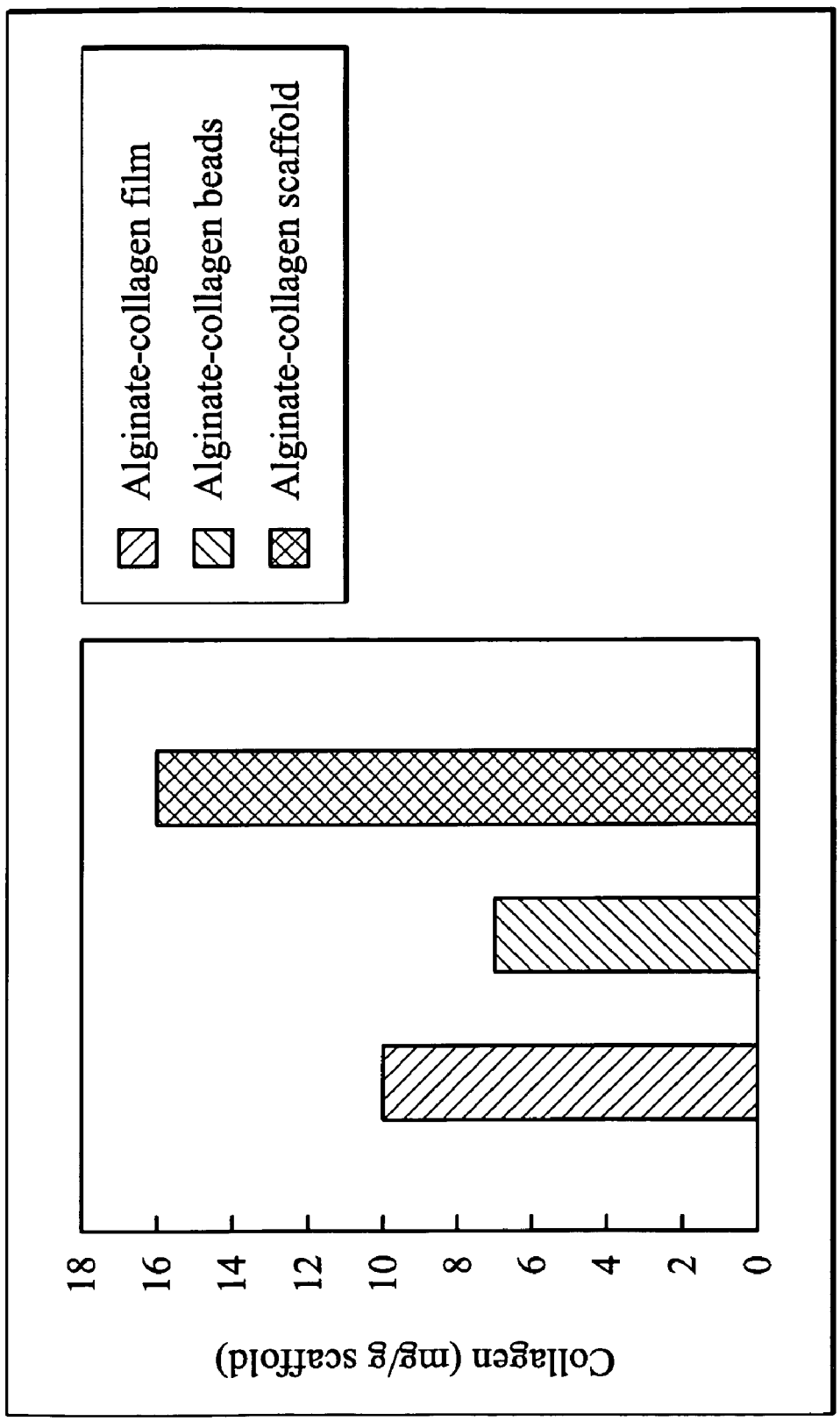
FIG. 4B is a diagram showing results of the ninhydrin determination.

Analysis is shown in FIG. 4B. The collagen content of the modified alginate film is 10 mg/g film, that of the microbeads is 7.3 mg/g microbead, and that of the porous matrix is 15.8 mg/g matrix.

Example 5

Cell Attachment and Growth

African green monkey kidney epithelial cells (Vero line) were maintained in DMEM supplemented with 10% FBS, sodium bicarbonate, and antibiotic-antimyotic at 37° C. in a 5% $CO_2$ incubator. The cells were incubated in a flat dish and passage thereof performed with trypsin when the cells were confluent. The cells were counted.

5-1: Cell Attachment and Growth in the Collagen-Modified Alginate Film

Figure 5:
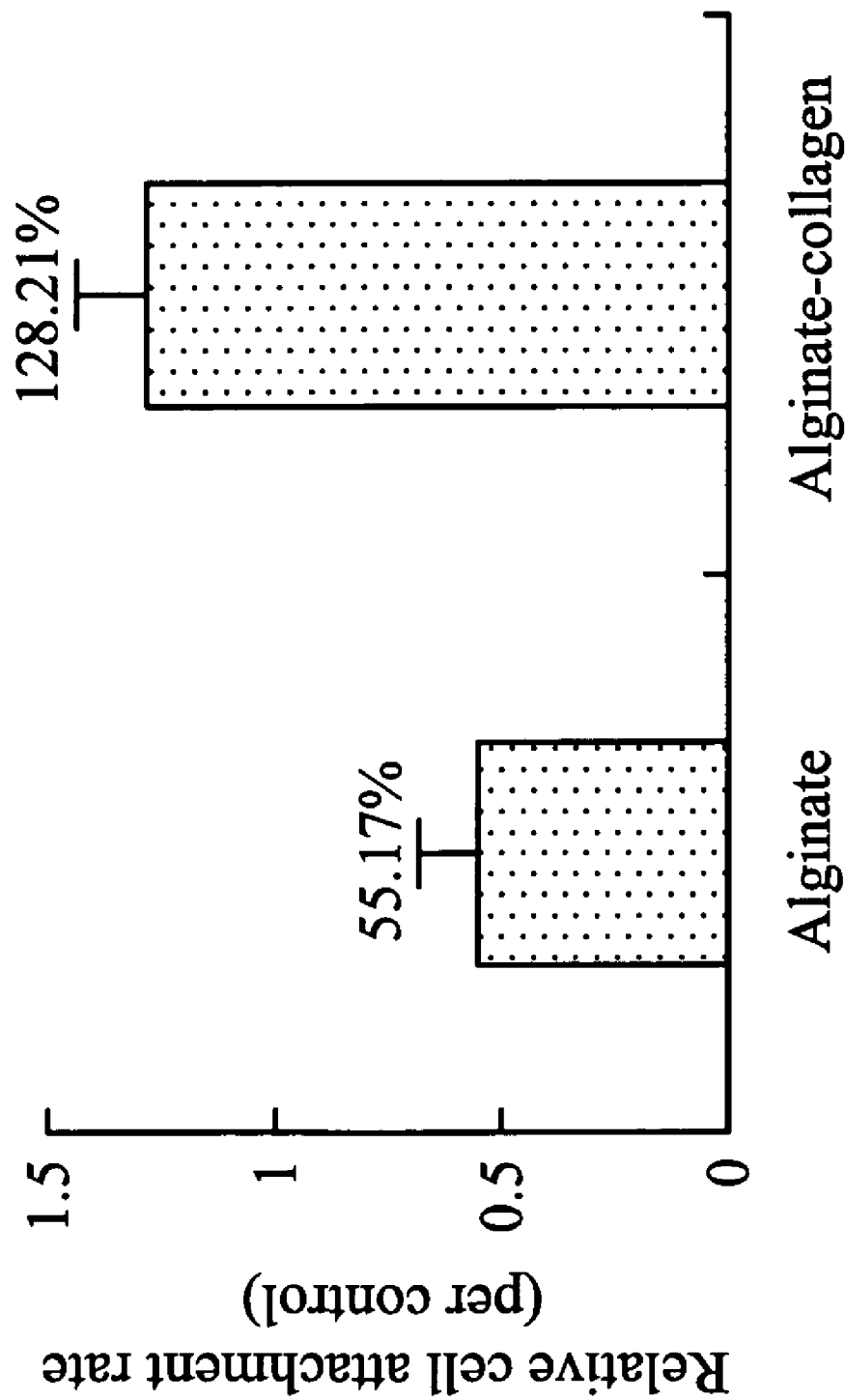
FIG. 5 is a diagram of the cell attachment rate of the film in the embodiment of the invention.
Figure 6A:
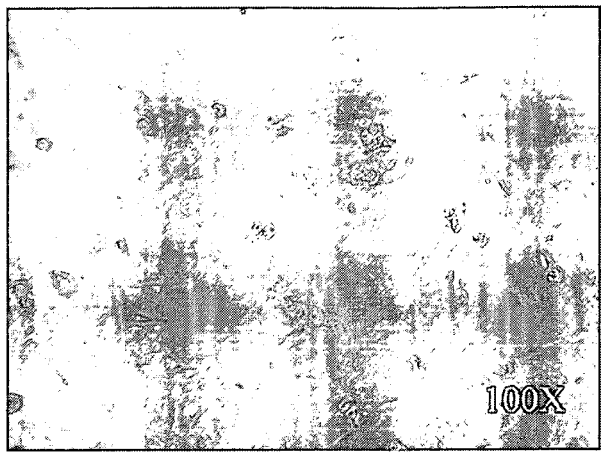
FIG. 6A~6F are microscopic photographs of the cell attachment on the film in the embodiment of the invention.
Figure 6B:
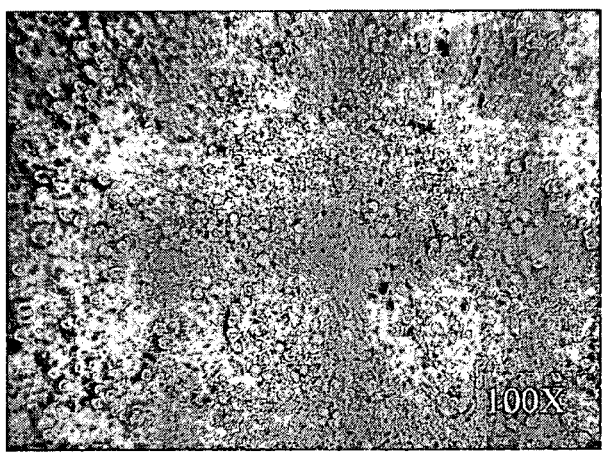
Figure 6C:
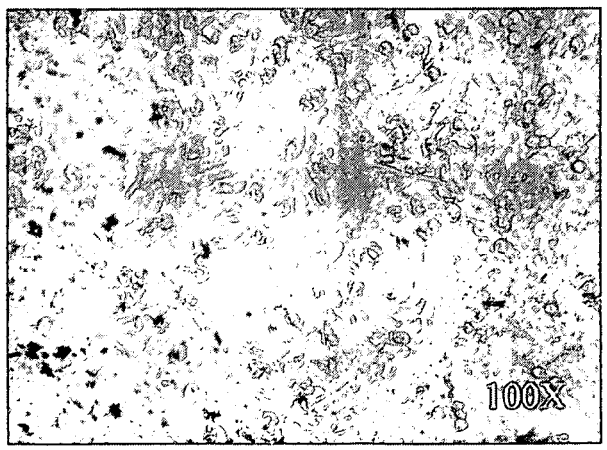
Figure 6D:
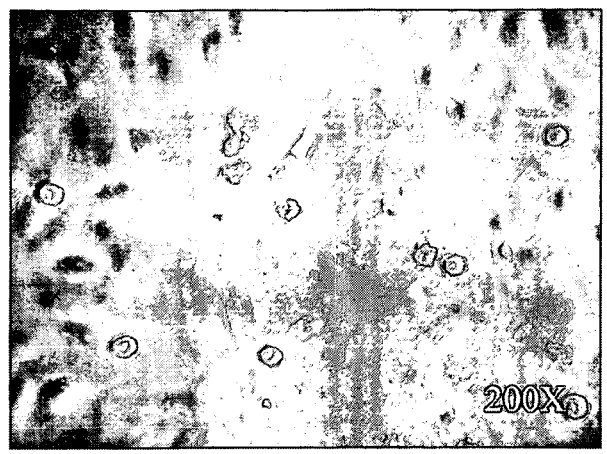
Figure 6E:
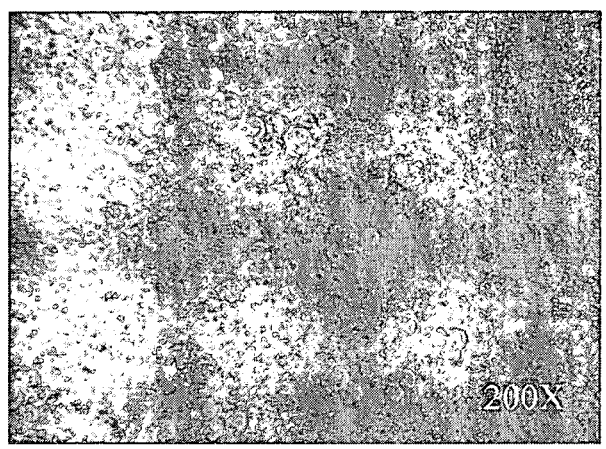
Figure 6F:
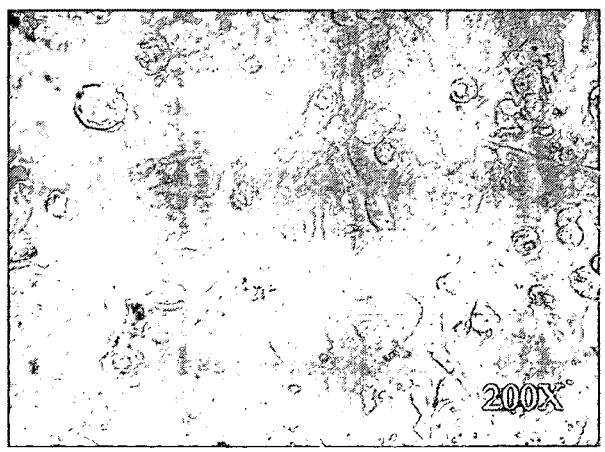
Figure 7A:
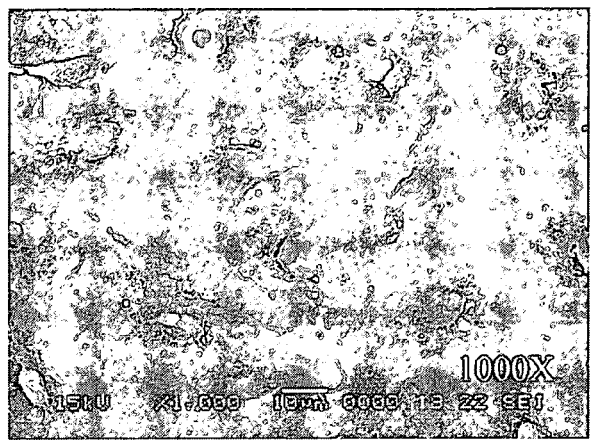
FIG. 7A~7C are scanning electron microscopic photographs of the cell attachment on the film in the embodiment of the invention.
Figure 7B:
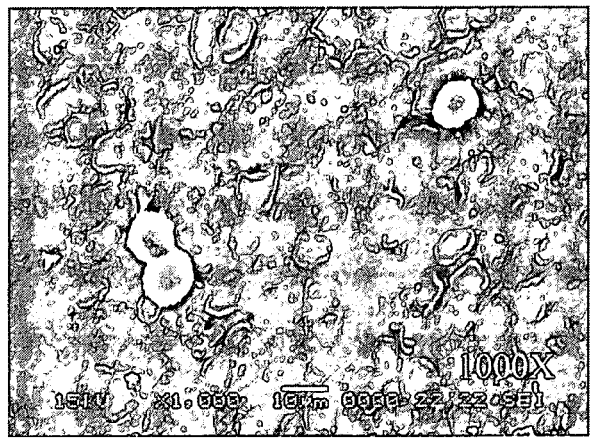
Figure 7C:
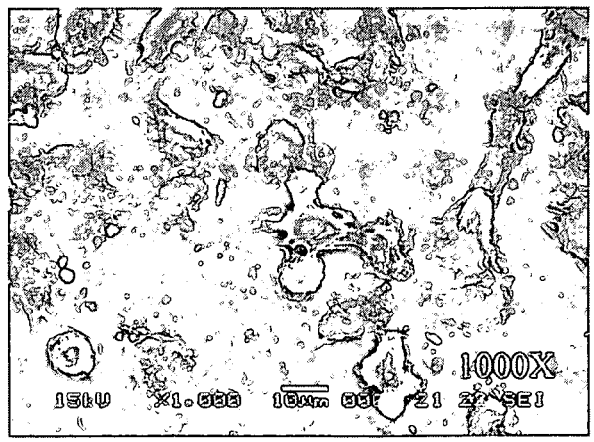

The sterilized films were washed with dd$H_2O$ 2 times and placed onto the wells of a plate. Vero cells in a density of $2.1 \times 10^5$/well were seeded into each well and incubated at 37° C. in a 5% $CO_2$ incubator for 6 hours. Cell attachment was observed under an optical microscope. The cells were counted with a hemocytometer. Cells cultured on the collagen-modified film were the experimental group, cells on unmodified film were the control group, and cells cultured on the well without any film were the blank control group, representing 100% attachment. The attached cell numbers of the experimental group and the control group were compared with the blank group, and results shown in FIG. 5. The cell attachment rate on the collagen-modified film for 6-hour cultivation was 128.21%, and that on the unmodified film was 55.17%. Cell attachment was observed under an optical microscope and a scanning electron microscope (SEM) and results shown in FIG. 6A~6F and FIG. 7A~7C, respectively. FIGS. 6A, 6D, and 7A are the blank control; FIGS. 6B, 6E, and 7B are the unmodified film; and FIGS. 6C, 6F, and 7C are the collagen-modified film. The results reveal that more unfolded Vero cells form on the collagen-modified film than on the unmodified film.

5-2: Cell Attachment and Growth in the Collagen-Modified Alginate Microbeads

Figure 8A:
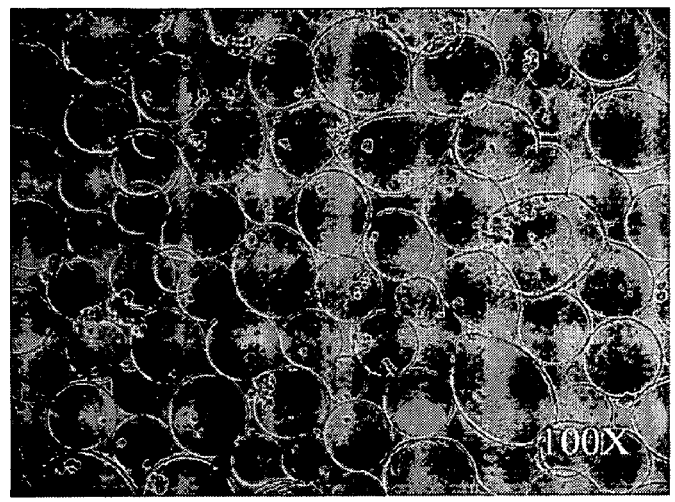
FIG. 8A~8F are microscopic photographs of the cell attachment on the microbeads in the embodiment of the invention.
Figure 8B:
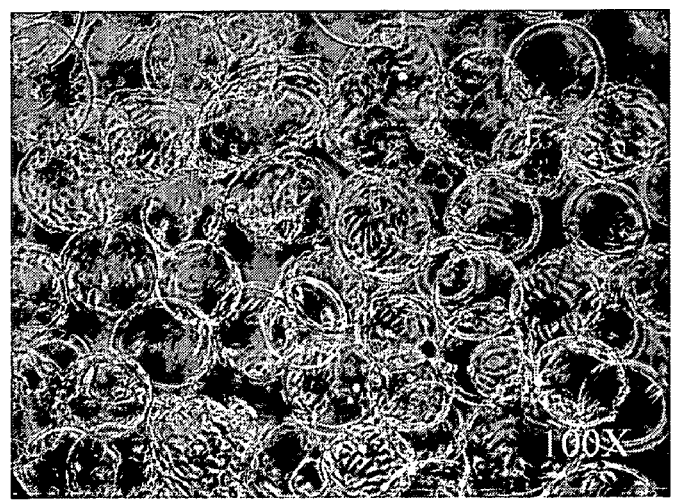
Figure 8C:
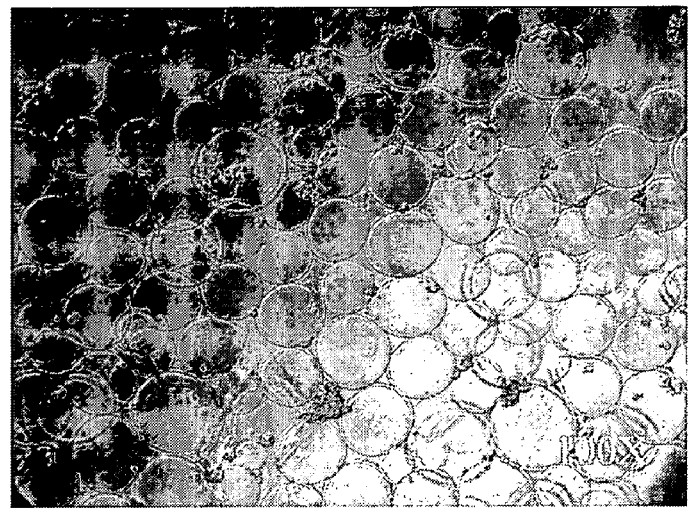
Figure 8D:
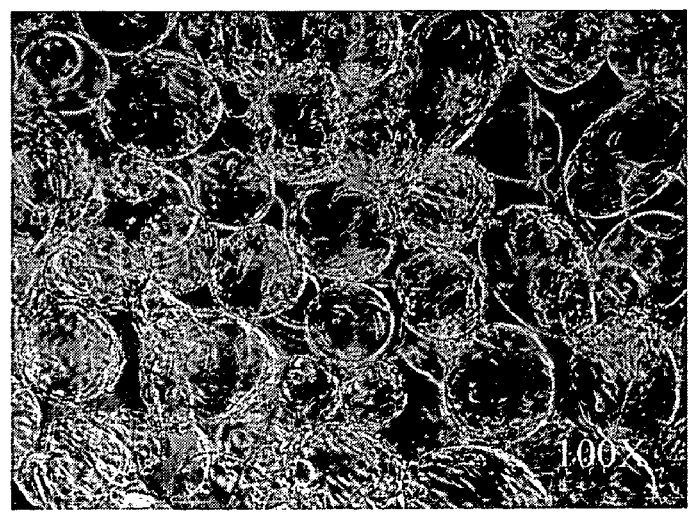
Figure 8E:
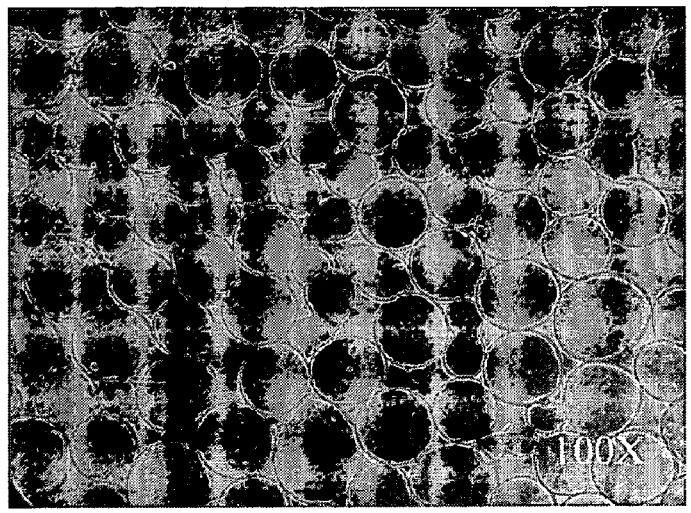
Figure 8F:
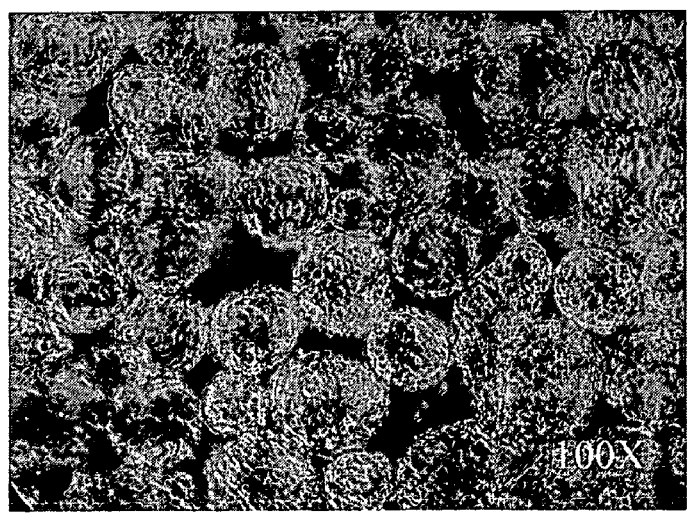

The sterilized microbeads were placed onto the wells of a plate. Vero cells in a density of $5 \times 10^5$/well were seeded into each well and incubated at 37° C. in a 5% $CO_2$ incubator for 1 day. The microbeads were moved to a new plate with fresh media for 2-, 3-, 7-day incubation. Cells cultured with the collagen-modified microbeads were the experimental group, and cells with the unmodified microbeads were the control group. Cell attachment was observed under an optical microscope and the results were shown in FIG. 8A~8F. FIGS. 8A, 8C, and 8E are the unmodified microbeads, and FIGS. 8B, 8D, and 8F are the collagen-modified microbeads. FIGS. 8A and 8B show 2-day incubation, FIGS. 8C and 8D show 3-day incubation, and FIGS. 8E and 8F show 7-day incubation. The results reveal that, on the second day of the incubation, Vero cells on the collagen-modified microbeads were completely attached, but cells on the unmodified microbeads were not fully attached. On the third day and the seventh day of the incubation, the cells on the collagen-modified microbeads apparently proliferated.

5-3: Cell Attachment and Growth in the Collagen-Modified Alginate Matrices

Figure 9:
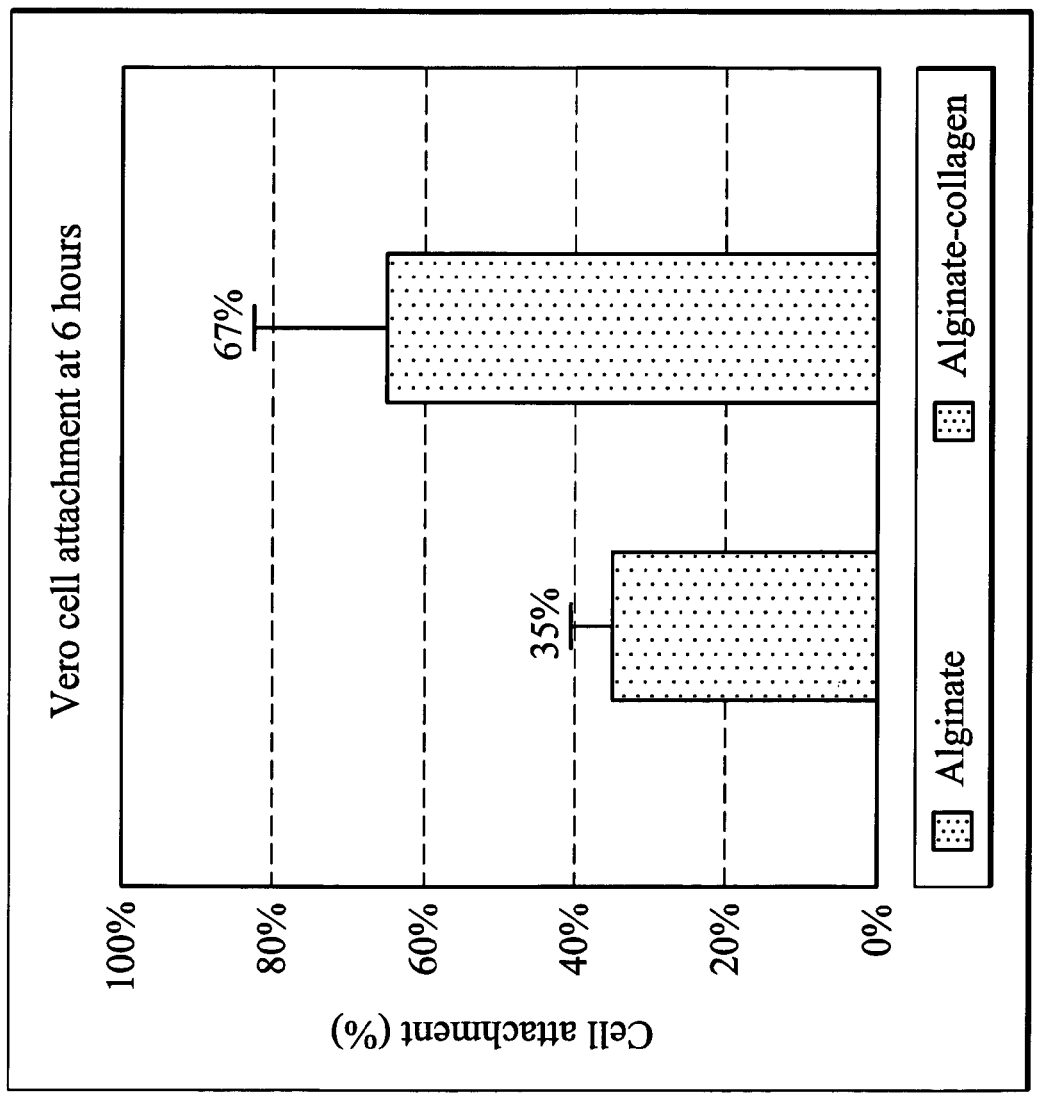
FIG. 9 is a diagram of the cell attachment rate on the porous matrix in the embodiment of the invention.

Eighty of the sterilized porous matrices were placed into a 50 ml centrifugation tube. $5 \times 10^6$ of Vero cells were suspended in 6 ml of medium and seeded into the prepared porous matrices. The cells were cultured in a static condition for 6 hours to be attached on the matrices. Cells cultured with the collagen-modified matrices were the experimental group, and cells with the unmodified matrices were the control group. After 6-hour static cultivation, unattached cells were washed out by fresh medium. The matrices were then dissolved with 100 mM of EDTA. Cells were counted and the cell attachment rate calculated. Results are shown in FIG. 9 and reveal that the cell attachment rate of the collagen-modified matrices is 67%, higher than that of the unmodified matrices (35%), indicating that the surface modification improves the cell attachment property of alginate matrix.

5-4: Growth Curve of Cells on the Collagen-Modified Film

The sterilized films were washed with dd$H_2O$ 2 times and placed onto the wells of a plate. Vero cells in a density of $2.1 \times 10^5$/well were seeded into each well and incubated at 37° C. in a 5% $CO_2$ incubator for 6, 24, and 72 hours. Cell attachment was observed under an optical microscope. The cells were counted with a hemocytometer. Cells cultured on the collagen-modified film were the experimental group, cells on unmodified film were the control group, and cells cultured on the well without any film were blank control group.

Figure 10A:
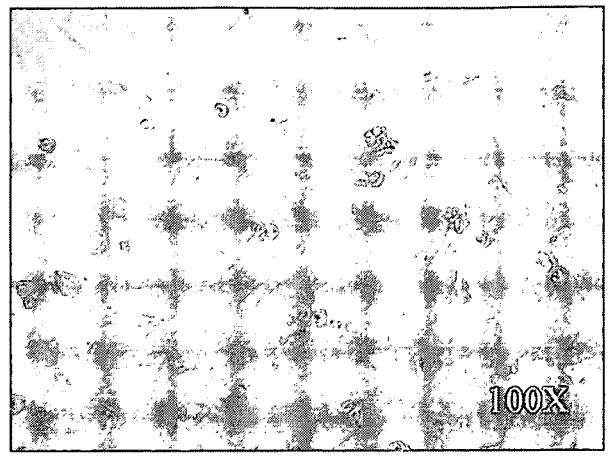
FIG. 10A~10I are microscopic photographs of the cell growth on the film in the embodiment of the invention.
Figure 10B:
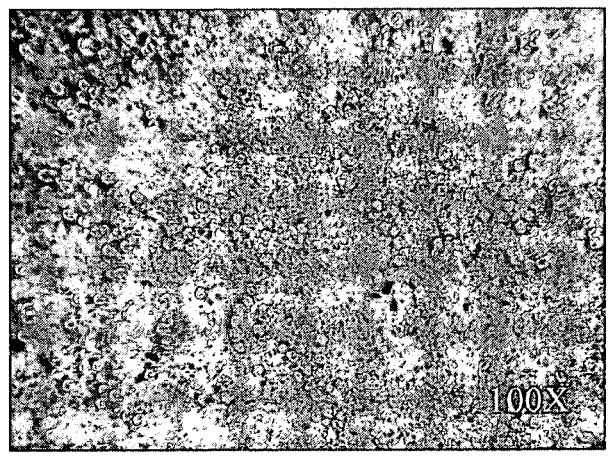
Figure 10C:
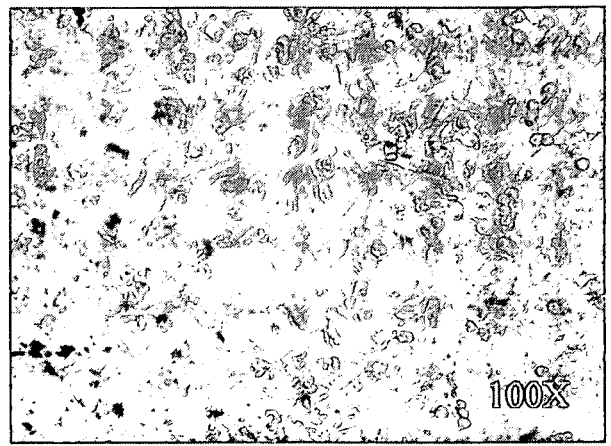
Figure 10D:
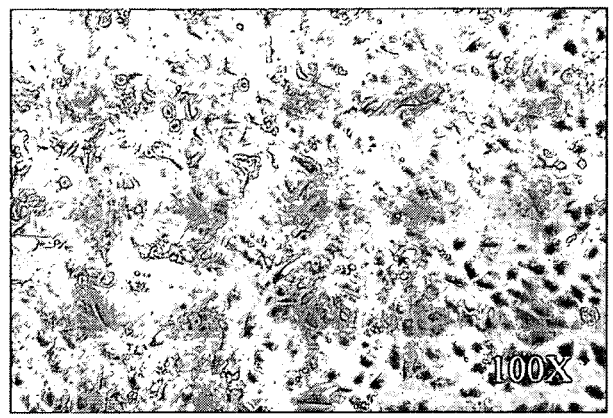
Figure 10E:
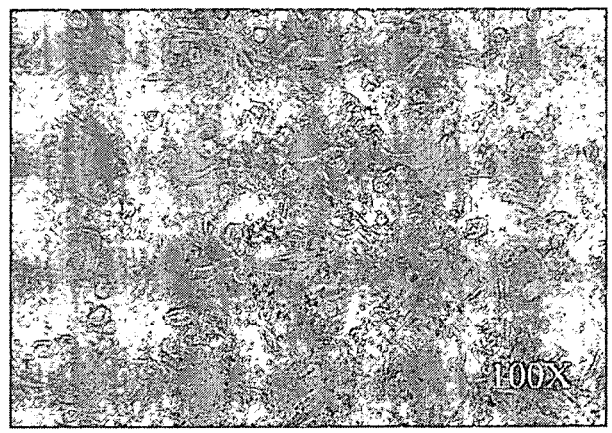
Figure 10F:
Figure 10G:
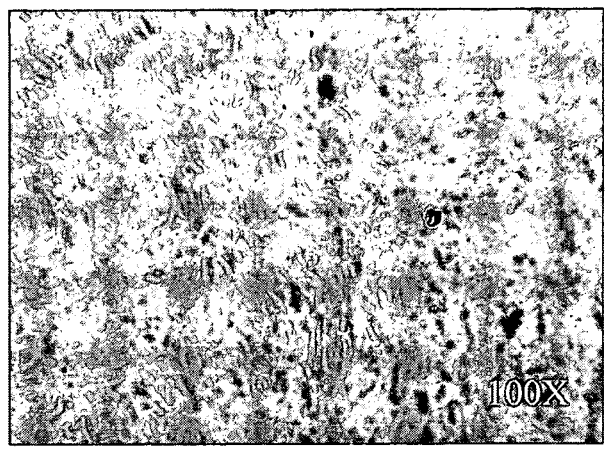
Figure 10H:
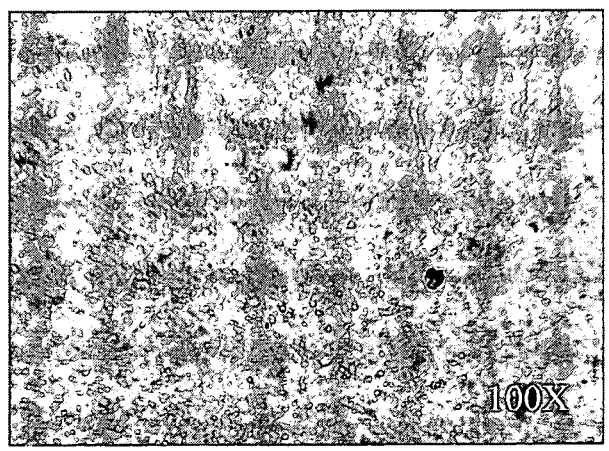
Figure 10I:
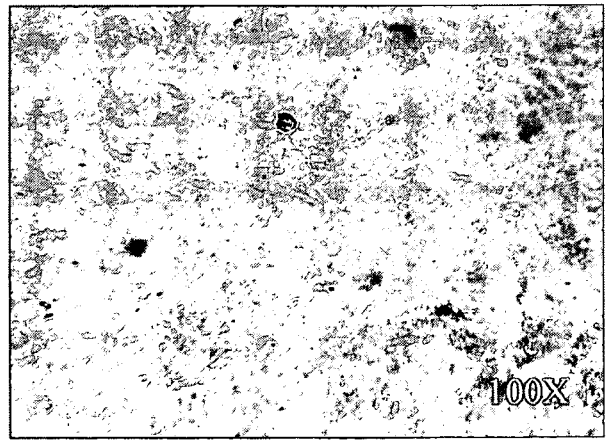

Vero cell growth was observed under an optical microscope. Results are shown in FIG. 10A~10I. FIGS. 10A, 10D, and 10G are the blank control, FIGS. 10B, 10E, and 10H are the unmodified film, and FIGS. 10C, 10F, and 10I are the collagen-modified film. FIGS. 10A, 10B, and 10C are 6-hour incubation, FIGS. 10D, 10E, and 10F are 24-hour incubation, and FIGS. 10G, 10H, and 10I are 72-hour incubation. The results reveal that, at the sixth hour, the growth and attachment of Vero cells cultured on the collagen-modified film were similar to that of the blank control, with improved attachment rate and morphology of cells cultured on the experimental group over the control group. After 24-hour incubation, the cells cultured on the experimental group proliferated. Cell number and morphology of the experimental group are similar to that of the blank control. The control cells were not observed in a good condition. After 72-hour incubation, cells of the blank control and the experimental group appeared as a monolayer, however, some cells of the control group became apoptosis.

Figure 11A:
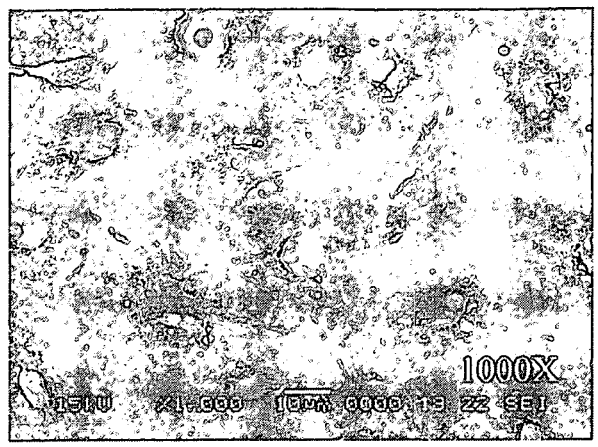
FIG. 11A~11I are scanning electron microscopic photographs of the cell growth on the film in the embodiment of the invention.
Figure 11B:
Figure 11C:
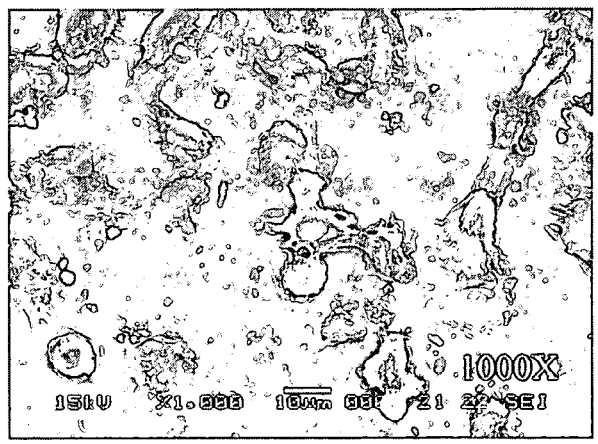
Figure 11D:
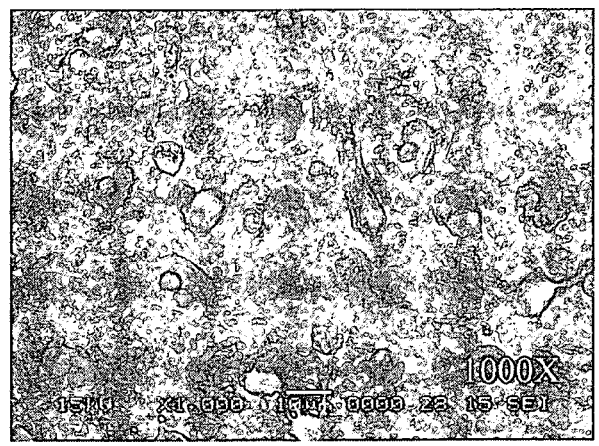
Figure 11E:
Figure 11F:
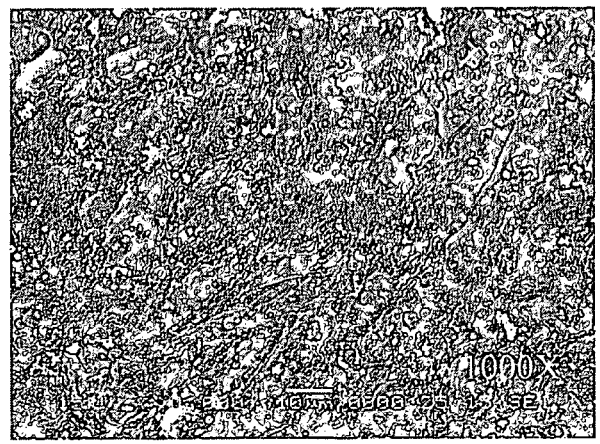
Figure 11G:
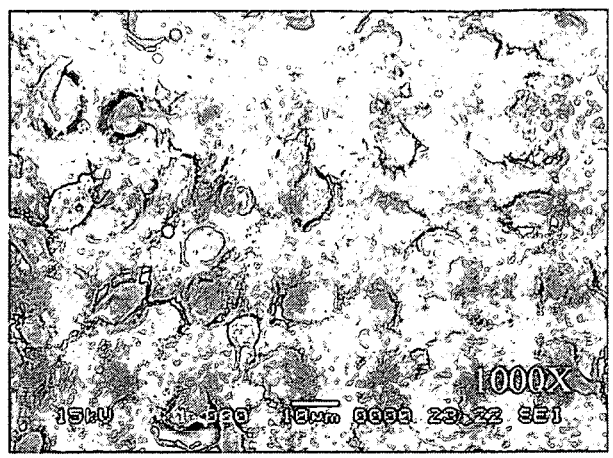
Figure 11H:
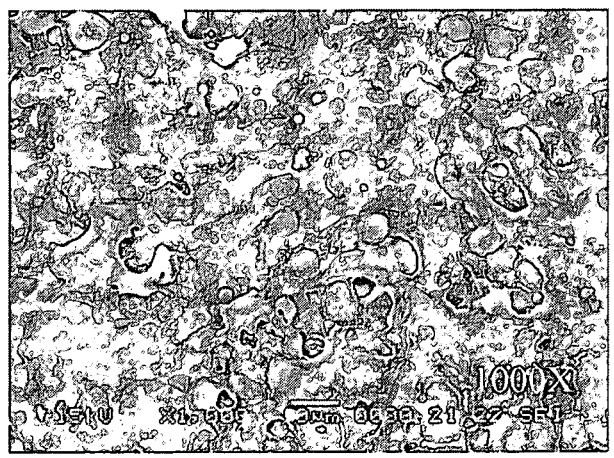
Figure 11I:
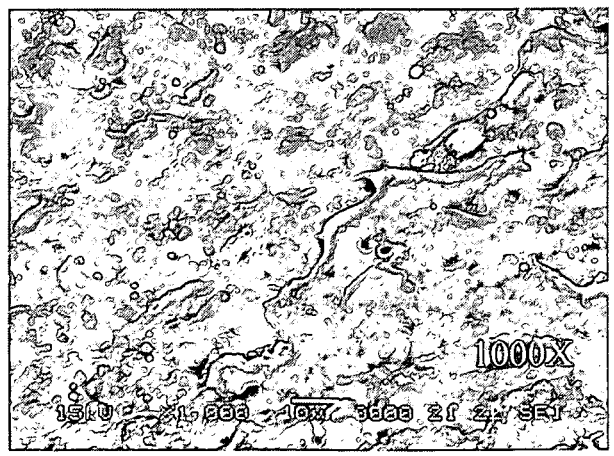

Vero cells were also observed under scanning electron microscope and results are shown in FIG. 11A~11I. FIGS. 11A, 11D, and 11G are the blank control, FIGS. 11B, 11E, and 11H are the unmodified film, and FIGS. 11C, 11F, and 11I are the collagen-modified film. FIGS. 11A, 11B, and 11C are 6-hour incubation, FIGS. 11D, 11E, and 11F are 24-hour incubation, and FIGS. 11G, 11H, and 11I are 72-hour incubation. The results reveal that, after 6-hour incubation, Vero cells cultured on the collagen-modified film were unfolded and spindle-shaped, and cells on the unmodified film were still round. After 24-hour incubation, the cells of the experimental group were completely unfolded and proliferated. Cell number and morphology of the experimental group were similar to that of the blank control. The control cells were partially unfolded and most of still round. After 72-hour incubation, cells of the blank control and the experimental group appeared as a monolayer, however, the control group showed fewer cells than the former two groups even with most unfolded.

Figure 12:
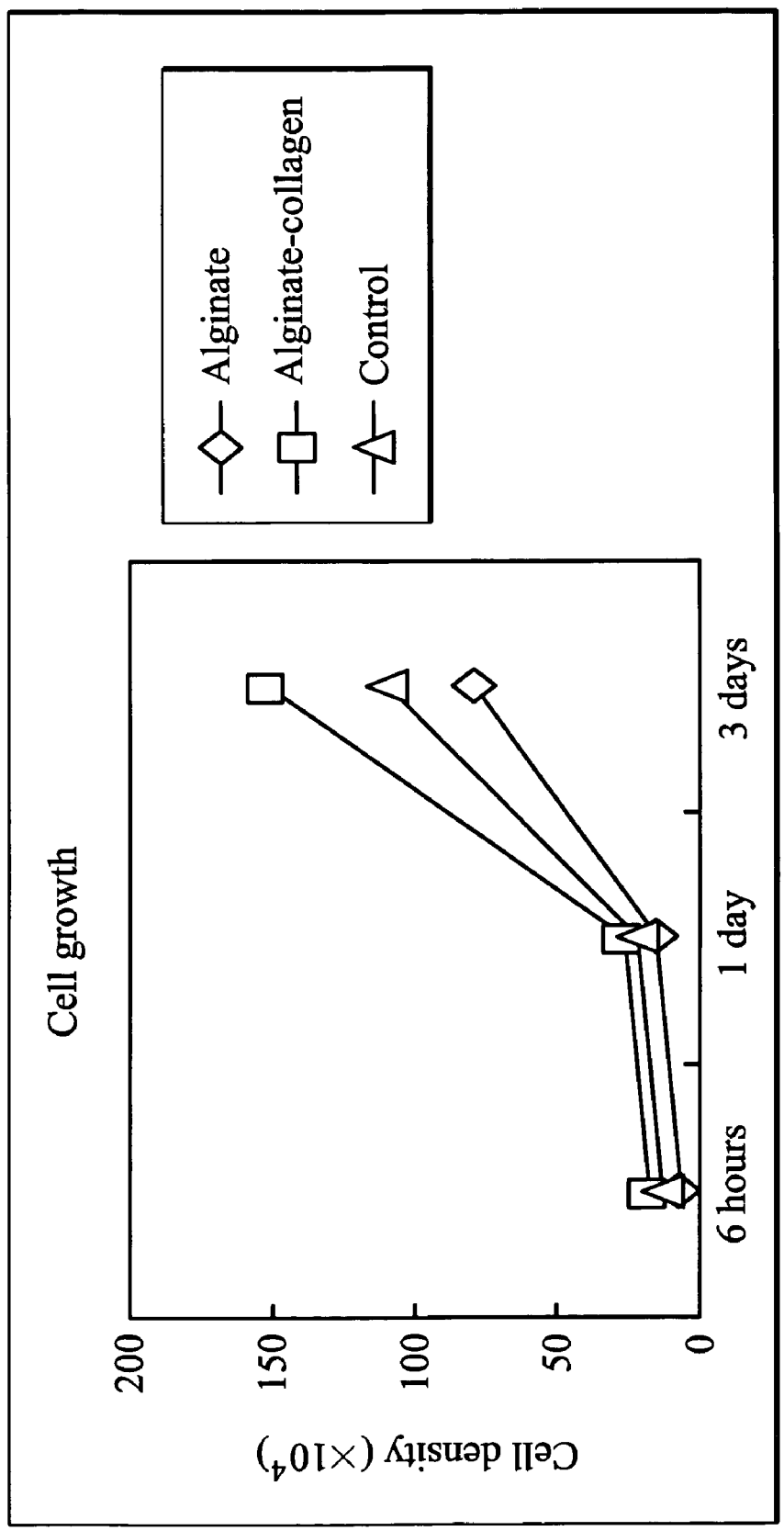
FIG. 12 is a diagram of the cell growth curve on the porous matrix in the embodiment of the invention.

The cells incubated for 6, 24, and 72 hours were collected and counted. The cell growth curve is shown in FIG. 12. The results reveal that, after 72-hour incubation, the experimental group has 1.5 times the cells of the blank control, with the control group was only slightly increased.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A surface modification method of polysaccharide, comprising:
    (a) immersing a solidified, crosslinked polysaccharide material in a 0.6 N HCl aqueous solution to protonize the solidified, crosslinked polysaccharide material;
    (b) after step (a), immersing the solidified, crosslinked polysaccharide material in an acetic acid solution containing a protein to mechanically embed the protein into the surface of the solidified, crosslinked polysaccharide material which is protonized; and
    (c) after step (b), immersing the solidified, crosslinked polysaccharide material in an alkaline solution containing bivalent metal ions to limit the embedded protein to the surface of the solidified, crosslinked polysaccharide material.

2. The method as claimed in claim 1, wherein the solidified, crosslinked polysaccharide comprises alginate, N,O-carboxymethyl chitosan, or carboxymethyl cellulose.

3. The method as claimed in claim 2, wherein the solidified, crosslinked polysaccharide is alginate.

4. The method as claimed in claim 1, wherein the solidified, crosslinked polysaccharide material is a film, a microbead, or a porous matrix.

5. The method as claimed in claim 4, wherein the polysaccharide material is a film with a thickness of 20 µm to 5,000 µm.

6. The method as claimed in claim 4, wherein the polysaccharide material is a microbead with a diameter of 20 µm to 2,000 µm.

7. The method as claimed in claim 4, wherein the solidified, crosslinked polysaccharide material is a porous matrix with a pore size of 20 µm to 2,000 µm.

8. The method as claimed in claim 4, wherein the solidified, crosslinked polysaccharide material is a porous matrix with a porosity of 30% to 95%.

9. The method as claimed in claim 1, wherein the protein comprises collagen, gelatin, or chitosan.

10. The method as claimed in claim 9, wherein the protein is collagen.

11. The method as claimed in claim 1, wherein the alkaline solution containing bivalent metal ions comprises calcium hydroxide, magnesium hydroxide, or strontium hydroxide solution.

12. The method as claimed in claim 11, wherein the alkaline solution containing bivalent metal ions is calcium hydroxide solution.

13. The method as claimed in claim 1, further comprising a step (d) of washing the solidified, crosslinked polysaccharide material with water after step (c).

14. A surface modification method of polysaccharide, comprising:
    (a) immersing a solidified, crosslinked alginate in a 0.6 N HCl aqueous solution to protonize the solidified, crosslinked alginate;
    (b) after step (a), immersing the solidified, crosslinked alginate in an acetic acid solution containing a collagen to mechanically embed the collagen into the surface of the solidified, crosslinked alginate which is protonized; and
    (c) after step (b), immersing the solidified, crosslinked alginate in a calcium hydroxide solution to limit the embedded collagen to the surface of the solidified, crosslinked alginate.

* * * * *